United States Patent [19]
Holtz

[11] Patent Number: 4,944,736
[45] Date of Patent: Jul. 31, 1990

[54] ADAPTOR CAP FOR CENTERING, SEALING, AND HOLDING A SYRINGE TO A BOTTLE

[76] Inventor: Leonard J. Holtz, 9474 Wayside Dr., Sunland, Calif. 91040

[21] Appl. No.: 375,504

[22] Filed: Jul. 5, 1989

[51] Int. Cl.[5] ........................ A61B 19/00; A61M 5/32; B65B 7/28

[52] U.S. Cl. .................................... 604/403; 604/411; 604/415; 215/200; 215/DIG. 3

[58] Field of Search ........................ 604/403, 411, 415; 141/330; 215/200, DIG. 3, 316, 317

[56] References Cited

U.S. PATENT DOCUMENTS 3,603,312 9/1971 Lucas .................................. 604/415
4,230,112 10/1980 Smith .................................. 604/403
4,349,024 9/1982 Ralston .................................. 604/403
4,671,331 6/1987 Pruden .................................. 604/415
4,685,917 8/1987 Baldini et al. ........................ 604/411

*Primary Examiner*—Mickey Yu
*Assistant Examiner*—Kerry Owens
*Attorney, Agent, or Firm*—Hadd S. Lane

[57] ABSTRACT

A means to connect a hypodermic syringe to its bottle of medicament, so that the syringe is in proper alignment to pierce the bottle sealing diaphragm. The means also holds the syringe to the bottle so that a measured amount of medicament may be withdrawn. Also included are sealing caps to retain full sterility of all elements during use and also non-use. The means permits the entire volume of the medicament to be withdrawn in a plurality of measured doses.

10 Claims, 3 Drawing Sheets

ADAPTOR CAP FOR CENTERING, SEALING, AND HOLDING A SYRINGE TO A BOTTLE

The objects of this invention are to provide an apparatus, or means, to connect quickly, accurately and easily, a hypodermic syringe to a medicament bottle, in particular a bottle of insulin; to penetrate centrally the rubber seal of the bottle so that the tip of the syringe is just beyond the seal; to hold the syringe and bottle in proper alignment so that a measured volume of medicament may be withdrawn; to permit removal of the syringe from the bottle for injection of the measured charge; and to provide caps to completely seal all the elements against contamination.

Using the syringe and bottle of the prior art, the user must try to penetrate the diaphragm of the bottle centrally with no guide or holding means, withdraw the fluid, and then trust to luck that no contamination occurs between dosages.

This invention comprises a plastic (or other material) connector between the bottle and the syringe which holds these parts in central alignment at the correct depth of penetration so that one hand can safely hold the assembly and the other hand can manipulate the syringe plunger to withdraw a measured volume of medicament.

The inventor, a diabetic himself, recognized the problem by direct experience, and finally worked out this solution, finding that it makes withdrawal of the insulin much simpler, safer, more sanitary, and more accurate, as the adaptor cap holds the bottle and syringe in proper and firm relationship, so that one hand holds both while the other operates the plunger of the syringe.

In application, the cap is installed semi-permanently on the top of the medicine bottle when it is first uncapped for use, and is left on the bottle for many usages, until the bottle is emptied. The cap has its own cap which closes the cap opening between fillings, thus keeping the medication clean and sterile. Since the inner surface of the cap is conical, the needle of the syringe is automatically guided into the center of the rubber diaphragm of the bottle each time a needle is introduced. The cap has a shoulder which abuts a shoulder on the syringe so that when fully inserted into the cap, the needle penetrates and projects very slightly beyond the diaphragm so that virtually all of the medicine can be withdrawn by successive doses.

The prior art system is much more intensive, less accurate in measuring of the dose, less sanitary, results in multiple random penetration of the rubber bottle seal, and usually leaves an unobtainable amount of medication in the bottle when the empty stage approaches. All of these disadvantages are eliminated by the cap of this invention.

IN THE DRAWINGS

Figure 1:
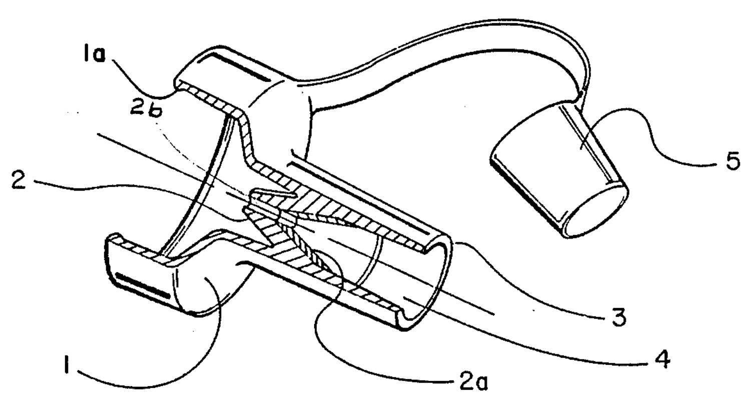
FIG. 1 shows an isometric cross-section of the cap of this invention.

In FIG. 1 the cap is shown with a body portion 1 from which a cylindrical portion **1*b* centrally rises and ends at shoulder 3. A flange projects downwardly from the body and ends in an inner bead 1*a*. The inner portion 1*b* includes an inner conical guide with a small central hole 2*b* that directs the needle 9 from any point in the entrance 4 of portion 1*b* to the smaller central opening therein and thence to the center of the diaphragm 7 of the medicine bottle 6. (See FIG. 2) This cone also has an inner lining 2*a* of a material sufficiently hard to prevent the sharpened needle 9 from scratching or penetrating the material of the cone as the needle is inserted into the cone and diaphragm. This liner may be a hard plastic, or a metal applied during or after the molding of the cap. When not in use, portion 1*b* is sealingly closed by cap 5**.

Figure 2:
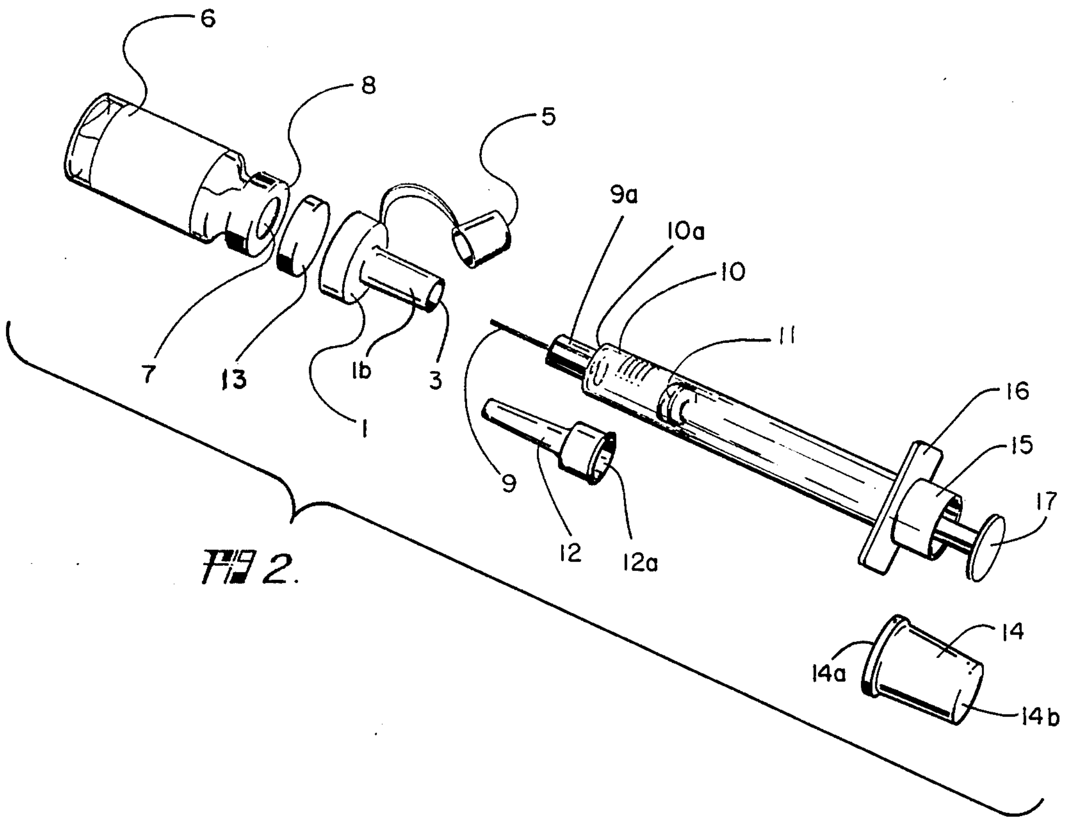
FIG. 2 is an exploded view of the syringe, cap, bottle, and also the auxiliary caps.
Figure 3:
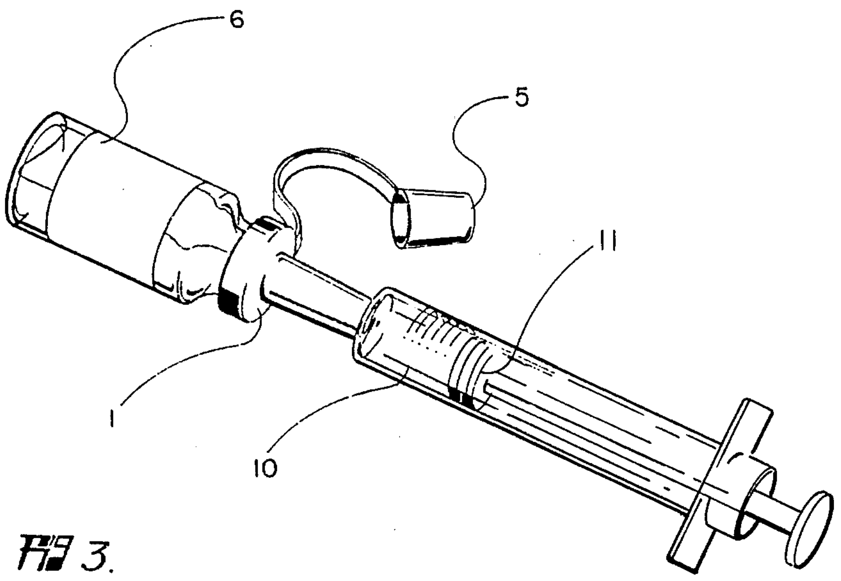
FIG. 3 is an assempled view of the syringe, cap, and bottle of this invention.

In FIG. 2, the original medicine bottle as purchased in a drug store is shown at 6. The bottle is sealed by a rubber (or other plastic) diaphragm 7 which is permanently sealed and held to the bottle by metal retainer 8. The usual cap for the bottle is shown at 13. The syringe 10 has the usual piston 11 operated by rod and finger piece 17. The needle 9 is carried by projection **9*a*, which is smaller than and attached to the barrel of syringe 10, there being a shoulder 10*a*** between the barrel and the projection.

In use the patient obtains a fresh bottle 6 of medicine and, in an atmosphere free of dust, aerosols, or germs, removes the cap 13. He then unwraps the adaptor cap 1 from its sanitary packaging and presses the flange of this cap over the metal retainer 8 of the bottle until the bead **1*a* snaps below the bottom of the retainer to secure, firmly but removably, the cap to the bottle. (See FIG. 5) The syringe 10, 9, etc., is furnished with auxiliary caps 12 and 14 (FIG. 2). Cap 12 will cover the needle 9, the portion 12*a* will sealingly and frictionally engage the projection 19, and will abut the soulder 10*a*. This fully protects the needle against both mechanical injury and contamination. Piston 11 will be fully inserted in the barrel 10 of the syringe so that finger piece 17 abuts the outer edge of cylinder 15, which is an integral part of the syringe. Cap 14 frictionally and sealingly engages the outer surface of cylinder 15 so that the end 14*b* holds the piston movement, and so that bead 14*a* of this cap abuts the lateral outer surface of second finger piece 16**.

Figure 5:
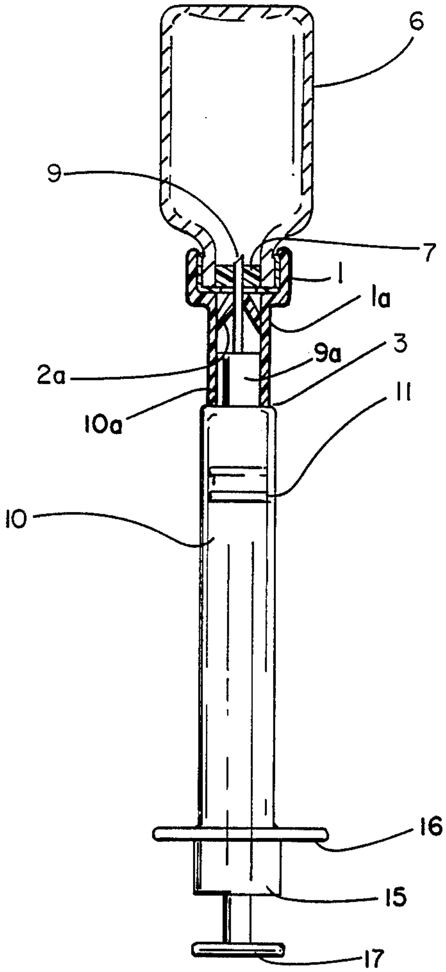
FIG. 5 is an enlarged view of the assembled cap and bottle, with certain parts in section to demonstrate its details more accurately.

The user then removes these auxiliary caps 12 and 14 and also 5 of the adaptor 1. He then inserts the needle 9 into the relatively large opening 4, and presses the bottle-adaptor and the syringe toward each other. The needle 9 is automatically guided to the central opening **2*a*. At this time projection 9*a* enters the opening 4 of the adaptor cap, which also centers and aligns all of the parts. Further pressing causes the needle 9 to penetrate diaphragm 7, until the shoulder 3 of the cap 1 abuts shoulder 10*a* of the syringe. The parts are dimensioned so that the needle 9 projects very slightly beyond the diaphragm 7 and into the bottle. This enables virtually all of the medicine to be withdrawn from the inverted bottle (See FIG. 5). Also the parts are frictionally, but firmly, secured together (FIG. 5). He then grasps the barrel 10 in one hand, inverts the bottle with the attached adaptor and with the other hand moves finger piece 17 and piston 11 downwardly the correct amount for one dose, as indicated by the graduation marks on the transparent syringe. The bottle 6, being firmly secured to the syringe 10 permits this manipulation. He then grasps the syringe in one hand and the bottle in the other, and pulls them apart. He then applies the medicine in the usual way by penetration of the needle and operation of the finger pieces 17 and 16. After withdrawal of the needle from his body, the user then reapplies the caps 12,14 and 5 of the adaptor. The adaptor 1** may remain on the bottle, since it is securely attached thereto, and also seals the bottle against contamination.

Figure 4:
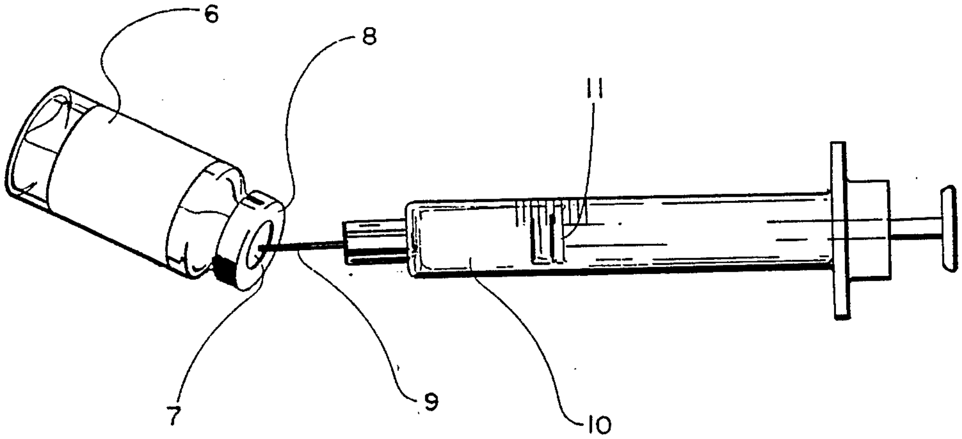
PRIOR ART FIG. 4.
FIG. 4 is an illustration of the prior art system of syringe and bottle only, illustrating the flexing, jamming, and sanitation problems inherent in this system.

FIG. 4 illustrates the prior art system. Thus only with great difficulty, and usually not at all, can the needle penetrate the center of diaphragm 7. Also, the needle usually enters at an angle, and the user cannot gauge the optimum depth of penetration. The repeated non-centered and angular projection of the needle causes multiple holes and rapid deterioration of the diaphragm. Also withdrawal of fluid from the bottle requires three hands—one for the bottle, one for the barrel 10 and one to operate the finger pieces 16 and 17. In an environment of motion, such as a moving automobile, boat, bus, train, aircraft, etc., these difficulties are substantially magnified.

With this invention, the assembly of the bottle and needle may be readily accomplished even though the vehicle motion is great. The small needle 9 may be easily placed in the large opening 4, and the parts are automatically centered, aligned, sealed and moved the correct distance by simple inward pressure.

The adaptor cap 1 and the syringe may be color-coded, to discriminate between medications when the patient is using more than one.

Since the cap 5 makes the assembled bottle and adaptor 1 completely sealed, and caps 12 and 14 make the syringe completely sealed, these two assemblies may be carried loose in a man's pocket, or a lady's handbag, with no fear of contamination. Since this is the simplest and most economical mode of carrying, it may be preferred by most users. The more fastidious may prefer a string-closed pouch of a chamois-like material to carry the parts. The most fastidious may prefer a fitted case containing perhaps two bottles, an adaptor, a fully capped syringe, and several needles, the case being closed and carried in a coat pocket or handbag.

Having described the preferred embodiment of my invention, I claim:

1. For use with a liquid-containing bottle having a perforatable closure diaphragm, and a syringe: an adaptor cap having means to attach said cap to the bottle above the diaphragm, said cap having a body and a hollow portion extending outwardly from said body and terminating in a larger opening, a guide portion spaced from said larger opening and having converging surfaces terminating in a smaller hole inwardly in said hollow portion, said syringe having a barrel, a projection fittable into said larger opening extending from said barrel and carrying a hollow needle, whereby a user may insert said needle into the larger opening of said hollow portion, and then into said smaller hole and into and through said diaphragm, while the syringe projection enters said larger opening and is retained therein, thereby causing the needle to be axially aligned and penetrate the diaphragm immediately below said hole and causing said syringe and bottle to be frictionally held together.

2. The adaptor cap of claim 1, wherein said hollow portion and said smaller hole are circular in right section, and said converging surfaces are conical.

3. The adaptor cap of claim 2, wherein the projection of said syringe is also circular and frictionally fits into said larger opening in said hollow portion.

4. The adaptor cap of claim 1, wherein said hollow portion terminates in an upper shoulder, there being a second shoulder on the projection of said syringe, the dimensions of the parts being such that when the syringe is fully inserted into the cap, the needle penetrates the diaphragm and extends a relatively short distance beyond to permit removal of substantially all of said liquid from said bottle by said needle.

5. The adaptor cap of claim 1, wherein the material of said converging guide surfaces is sufficiently hard to prevent penetration or scratching thereof by said needle.

6. The adaptor cap of claim 1, wherein said converging surfaces are formed by a separate piece of a material hard enough to resist scratching or penetration by said needle.

7. The adaptor cap of claim 3 wherein the said hollow portion has an auxiliary cap to seal and close said larger opening therein, and the syringe has an auxiliary sealing cap to engage said projection and cover said needle.

8. The adaptor cap of claim 6, wherein said separate piece is made of a material selected from the group consisting of hard plastics and soft metals, and the cylindrical portion is made from a softer, resilient plastic.

9. The adaptor cap of claim 1, wherein said diaphragm is secured to said bottle by a retainer having a cylindrical portion surrounding the opening of said bottle, the said means to attach said cap to the bottle comprising a flange extending downwardly from said body surrounding the retainer cylindrical portion, and having a bead which resiliently engages below said last mentioned portion, thus producing a firm, but removable connection.

10. The adaptor cap of claim 1 wherein the said hollow portion is cylindrical to frictionally retain the projection of the syringe.

* * * * *